United States Patent [19]

Masaki

[11] 4,062,364

[45] Dec. 13, 1977

[54] ELECTRODE FOR USE IN LOW FREQUENCY ELECTRONIC THERAPY DEVICE

[76] Inventor: Kazumi Masaki, 7-3, 4-chome Fujishirodai, Suita, Osaka, Japan

[21] Appl. No.: 616,669

[22] Filed: Sept. 25, 1975

[30] Foreign Application Priority Data

June 30, 1975  Japan .................. 50-9210[U]

[51] Int. Cl.$^2$ ............................................. A61N 1/18
[52] U.S. Cl. ................................. 128/405; 128/422
[58] Field of Search .................. 128/404–411, 128/416–418, 419 R, 422, 303.14, 420, 421

[56] References Cited

U.S. PATENT DOCUMENTS

| | | | |
|---|---|---|---|
| 791,730 | 6/1905 | Stanger | 128/409 |
| 1,740,240 | 12/1929 | Honey | 128/408 |
| 2,808,826 | 10/1957 | Reiner et al. | 128/422 |
| 3,533,397 | 10/1970 | Scher | 128/405 |
| 3,543,761 | 12/1970 | Bradley | 128/418 |
| 3,642,008 | 2/1972 | Bolduc | 128/416 |
| 3,987,795 | 10/1976 | Morrison | 128/303.14 |

FOREIGN PATENT DOCUMENTS

| | | | |
|---|---|---|---|
| 13,888-70 | 10/1971 | Australia | 128/417 |
| 65,169 | 1/1956 | France | 128/404 |
| 637,019 | 10/1926 | France | 128/417 |
| 962,695 | 7/1964 | United Kingdom | 128/422 |

*Primary Examiner*—John D. Yasko
*Assistant Examiner*—Lee S. Cohen
*Attorney, Agent, or Firm*—Bucknam and Archer

[57] ABSTRACT

There is disclosed an electrode construction for use in a low frequency electronic therapy device and adapted to be brought in contact with the skin at a therapy point of a human being. A negative electrode is adapted to have a contacting area between the negative electrode and the skin which is larger than that between a positive electrode and the skin. Each of the electrodes has a hollow hemispherical metal member adapted to store water in the hollow chamber. The stored water exudes little by little through perforations provided through the hollow hemispherical metal member to impregnate an outer water-impregnating cover applied to cover the hemispherical metal member.

6 Claims, 12 Drawing Figures

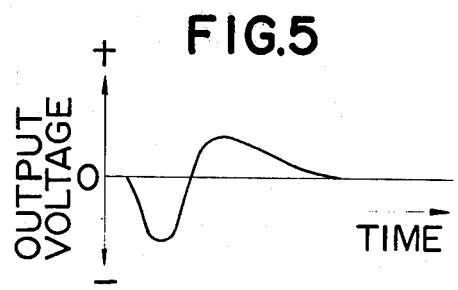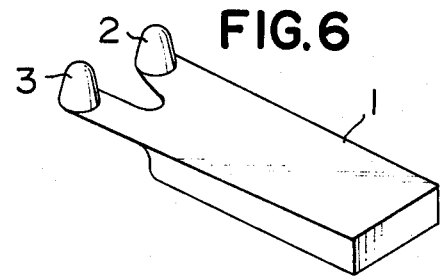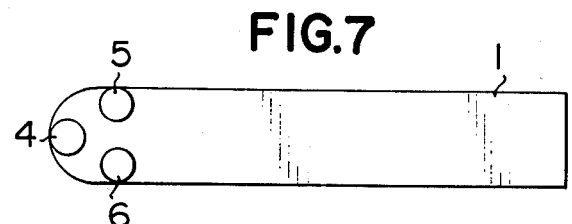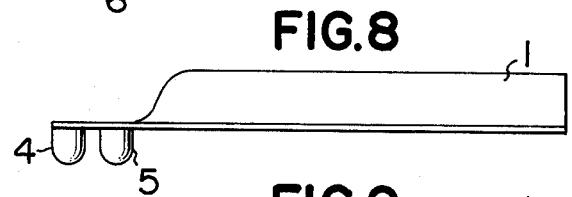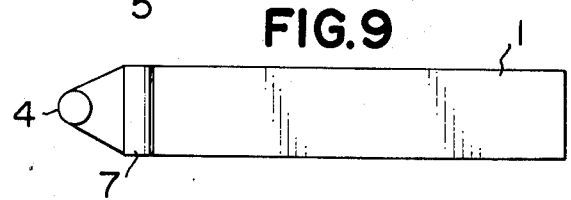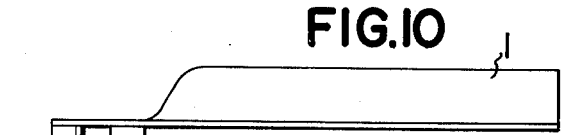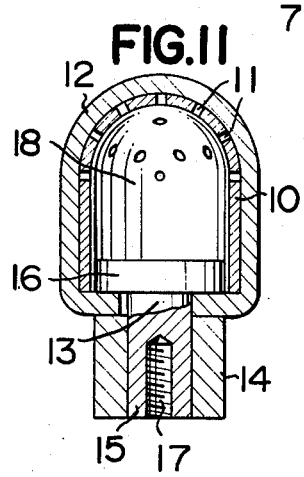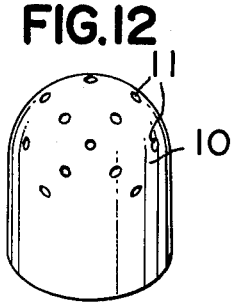

ELECTRODE FOR USE IN LOW FREQUENCY ELECTRONIC THERAPY DEVICE

This invention relates to a low frequency electronic therapy device, and more particularly to an electrode construction for use in the electronic therapy device and adapted to be brought in contact with a therapy point of a warm-blooded animal to give electric stimulus thereto.

Heretofore, there have been well-known different types of low frequency electronic therapy devices adapted to apply to a therapy point of a warm-blooded animal such as a human being, a low frequency electric stimulus having a frequency and a waveform substantially similar to those of a "nerve induced voltage" caused when a stimulus is given to nerve fibers of the warm-blooded animal. Many of the conventional low frequency electronic therapy devices have two electrodes adapted to be contacted with a therapy point to apply a low frequency electric stimulus thereto.

In therapy using the conventional electronic therapy device, a human being feels pain in the skin under the electrode through which a negative voltage is applied. Each of the electrodes used in the electronic therapy devices has been adapted to be impregnated with water to obtain good electric contact between the electrode and the skin. However, since the conventional electrodes dry up in a very short period, the electrodes must often be impregnated with water during therapy.

It is, therefore, one object of the present invention to eliminate the above-mentioned defects of the conventional low frequency electronic therapy device.

It is another object of the present invention to provide a low frequency electronic therapy device having electrodes adapted to decrease the pain felt by a human being.

It is a further object of the present invention to provide a low frequency electronic therapy device having electrodes which do not require frequent impregnation with water.

These and other objects of the present invention are attained by means of a low frequency electronic therapy device having two electrodes wherein one electrode through which a negative voltage is applied to the skin of a therapy point has a contacting area larger than that of the other electrode. Alternatively, the electronic therapy device has a negative electrode consisting of at least two electrodes, each of which is the same as the positive electrode, so that the total contacting area of the negative electrode against the skin is at least twice that of the positive electrode. Each of the electrodes may comprise a hollow hemispherical conductive member having a plurality of perforations and a water-impregnating cover made from a material such as sponge and cloth and applied to cover the outer surface of the conductive member so that water is stored in the hollow chamber in the conductive member and exudes little by little through the perforations to impregnate the outer water-impregnating cover, whereby the outer cover is ceaselessly impregnated with water to keep good electric contact between the electrode and the skin at the therapy point.

For a better understanding of the invention as well as other objects and further features thereof, preferred embodiments of the invention will be explained with reference to the accompanying drawings in which:

FIG. 5 shows a waveform of an output from the oscillating circuits shown in FIGS. 1 and 4;

FIG. 6 is a diagramatically perspective view of the conventional low frequency electronic therapy device showing the arrangement of electrodes;

FIG. 7 is a diagramatical bottom view of the low frequency electronic therapy device showing a first embodiment of the electrode construction according to the present invention;

FIG. 8 is a side view of the device shown in FIG. 7;

FIG. 9 is a diagramatical bottom view of the low frequency electronic therapy device showing a second embodiment of the electrode construction according to the present invention;

FIG. 10 is a side view of the device shown in FIG. 9;

FIG. 11 is a sectional view of the electrode used in the devices shown in FIGS. 7 to 10; and FIG. 12 is a perspective view of an inner member of the electrode shown in FIG. 11.

Figure 1:
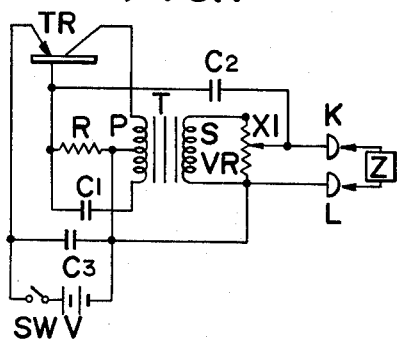
FIG. 1 is a circuit diagram showing one example of an oscillator for use in the conventional low frequency electronic therapy device.

For a general understanding of the illustrated low frequency electronic therapy device, some examples of the device are now explained with reference to FIGS. 1 to 6. Referring to FIG. 1, there is shown an oscillating circuit having a stabilized oscillating frequency for use in a low frequency electronic therapy device. As seen from the drawing, the oscillating circuit is a blocking oscillator of the transformer coupling type in which an output is taken out from the secondary winding S of the coupling transformer T. The secondary winding S of the transformer T is connected in parallel to an output adjusting variable resistor VR, a variable terminal Xl of which is connected to one of electrodes K. To the other electrode L is connected one end of the secondary winding S. These electrodes K and L are adapted to be pushed on the skin at a therapy point in a warm-blooded animal such as a human being.

Since the blocking oscillator as shown in FIG. 1 is well-known, an explanation of the construction and operation is here omitted, but explanation is now made about portions which are not provided in the fundamental type of the blocking oscillator.

The oscillating circuit shown in FIG. 1 has a capacitor $C_2$ provided to prevent the variation of oscillating frequency caused partially by the change in the contacting resistance between the electrode and the skin and partially by the adjustment of the output adjusting variable resistor VR. The contacting resistance between the electrode and the skin, i.e., the load resistance Z varies between a few ten thousand ohms when the electrode is lightly pushed onto the skin at the therapy point and a few thousand ohms when the electrode is strongly pushed onto the skin. When the load resistance Z is large, namely when the load is small, the voltages at the primary winding P and at the secondary winding S become large, respectively. Such a large voltage at the primary winding is applied to the capacitor $C_1$ to charge it. A discharge of the capacitor which was charged with such a large voltage requires a long time, and this lowers the oscillating frequency of the blocking oscillator. On the other hand, when the load resistance Z is small, the oscillating frequency becomes high. As seen from the above, the oscillating frequency of the blocking oscillator is changed by the change in the pushing pressure of the electrode to the skin. Furthermore, the oscillating frequency is varied due to adjustment of the output adjusting variable resistor VR for the same reason. However, the variation in the oscillating frequency is undesirable because it means that the frequency of the electric stimulus applied to the therapy point is shifted from the ideal frequency of nerve induced voltage.

Figure 2:
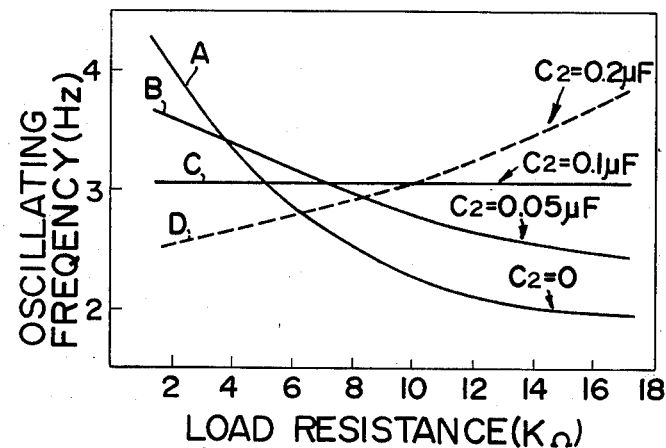
FIG. 2 is a graph showing the relationship between the oscillating frequency and change in load resistance at various capacitances for one capacitor used in the oscillating circuit shown in FIG. 1.
Figure 3:
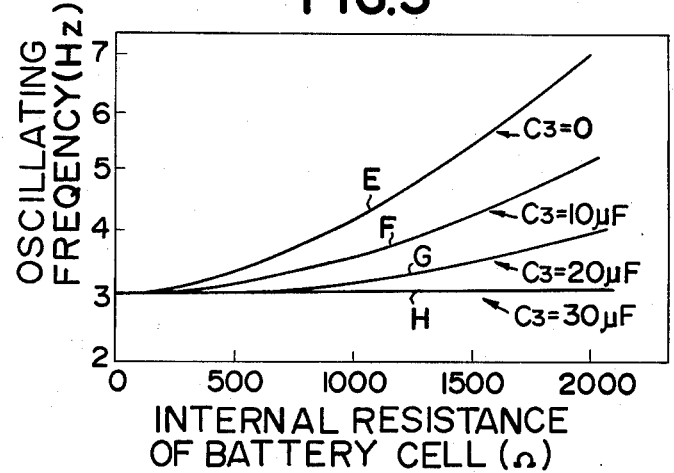
FIG. 3 is a graph showing the relationship between the oscillating frequency and change in internal resistance of the battery cell at various capacitances for another capacitor used in the oscillating circuit shown in FIG. 1.

Referring to FIG. 2, the curved line A shows the relationship between the oscillating frequency and the load resistance when the capacitor $C_2$ is not provided. In this case, the oscillating frequency changes between 4 Hz and 2 Hz by the change of the load resistance between 2 K$\Omega$ and 16 K$\Omega$. When the capacitor $C_2$ is 0.05 $\mu$F, the frequency varies between 3.5 Hz and 2.5 Hz as shown by the curved line B in FIG. 2. When $C_2$ is 0.1 $\mu$F, the device oscillates at about 3 Hz without substantial frequency variation. As shown by the line D in FIG. 2, when the capacitor $C_2$ is 0.2 $\mu$F, the frequency varies between 2.5 Hz and 3.5 Hz, but the frequency is low when the load resistance is low while frequency is high when the resistance is high. Thus, the device oscillates without frequency variation at $C_2 = 0.1$ $\mu$F.

This frequency stabilization is considered to be due to the fact that when the load resistance is large, the capacitor $C_1$ is charged with a high voltage to store a large amount of charge, and the charge stored in the capacitor $C_1$ is discharged through the resistor $R_1$ and at the same time the charge is discharged through the capacitor $C_2$ and the variable resistor VR to prevent the oscillating frequency from lowering. Therefore, by suitably selecting the capacitance of the capacitor $C_2$, the oscillating frequency can be stabilized.

The oscillating circuit shown in FIG. 1 also has a capacitor $C_3$ provided to prevent the variation of oscillating frequency caused by the change in the internal resistance of the battery cell for driving the circuit. If the capacitor $C_3$ is not provided, upon increase in the internal resistance of the battery cell, the oscillating frequency increases, for example, from 3 Hz to 8 Hz as shown by the curved line E of FIG. 3. This is undesirable for the reason as mentioned hereinbefore. When the capacitor $C_3$ is 10 $\mu$F, the oscillating frequency varies from 3 Hz to about 5 Hz as shown by the curved line F. When the capacitor $C_3$ is selected at 20 $\mu$F, the frequency varies from 3 Hz to about 4 Hz as shown by the line G. When the capacitor $C_3$ is 30 $\mu$F or more, even if the internal resistance of the battery cell becomes 2000 ohms, the oscillating frequency is not substantially changed as shown by the line H of FIG. 3. This frequency stabilization is due to the fact that the time constant required to charge the capacitor $C_3$ with the battery cell V which is the product of the capacitance of the capacitor $C_3$ and the internal resistance of the battery cell is on the order of one-hundredth second and is very short compared with the blocking oscillating period ($1/f = \frac{1}{3}$ second), and therefore the capacitor $C_3$, not the battery cell, can supply the blocking oscillating circuit with the amount of electricity required for one blocking oscillation.

As seen from the above, by the provision of the capacitors $C_2$ and $C_3$, the oscillating circuit oscillates at a constant frequency irrespective of the variation in the load resistance and the change in the internal resistance of the battery cell.

Figure 4:
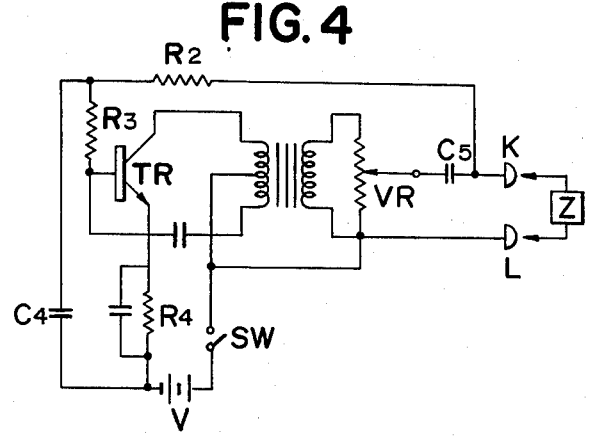
FIG. 4 is a circuit diagram showing an oscillating circuit for use in the conventional switchless low frequency electronic therapy device.

Next, referring to FIG. 4, there is shown an electric circuit diagram of a switchless low frequency electronic therapy device. This circuit is adapted to be energized only when electrodes K and L are brought in contact with the skin of a human being. Namely, when the electrodes are contacted with the skin at a therapy point, an electric current flows from a battery cell V through a switch SW, the electrode L, the skin (the load resistance Z), the electrode K, resistors $R_2$ and $R_3$, the base-emitter junction of the transistor TR, and a resistor $R_4$, so that a base bias is given to the transistor TR. As a result, the circuit causes blocking oscillation. However, when the electrodes are disengaged from the skin, the electric current as mentioned above does not flow, and therefore, the base bias is interrupted to cut off the transistor TR. Thus, the collector current is interrupted and the circuit stops the blocking oscillation. A capacitor $C_4$ is provided as a filter which prevents the alternating current occurring at the electrode K from being applied to the base of the transistor TR through the resistors $R_2$ and $R_3$ so that a base bias voltage having minimum pulsation is applied to the base of the transistor. A capacitor $C_5$ is provided to pass only the alternating voltages to the electrodes. As seen from the above, even if the user forgets to open the switch SW after the use of the device, since the electrodes K and L are not in engagement with the skin, the circuit does not operate, and therefore the battery cell is prevented from being consumed.

The output voltage from the blocking oscillating circuits shown in FIGS. 1 and 4 takes a pulse voltage waveform wherein each pulse is constituted by a voltage that firstly goes negative and then crosses zero to go positive as shown in FIG. 5. In the conventional low frequency electronic therapy device, such output voltage is applied to the skin at a therapy point through two electrodes 2 and 3 which are provided on one end of an electronic therapy device housing 1 as shown in FIG. 6 and which are connected, for example, to the output terminals K and L of the oscillating circuits shown in FIGS. 1 and 4. When the two electrodes 2 and 3 are brought in contact with the skin at a therapy point, pain is felt in the skin which is contacted with the electrode through which the negative voltage as shown in FIG. 5 is applied. Particularly, in the case that the negative voltage is equal to the positive voltage, larger pain is felt when the negative voltage is applied. The cause of this pain is considered to be related to the current density of the current flowing through the skin. In the present invention, accordingly, the surface area of the electrode through which the negative voltage is applied is made larger than that of the other electrode so that the contacting area between the skin and the electrode through which the negative voltage is applied is made larger to thereby make smaller the current density of the current flowing through the skin.

Referring to FIGS. 7 and 8, there is shown one embodiment of the electrode construction according to the present invention. Three identical electrodes 4, 5 and 6 are provided on one end of the device housing 1. The electrode 4 is connected to the output terminal L of the blocking oscillating circuit, and the electrodes 5 and 6 are connected together to the output terminal K through which the negative voltage is applied. Therefore, the total contacting area of the electrodes 5 and 6 through which the negative voltage is applied is twice that of the positive electrode 4. In this case it has been found that the pain felt by a human being is decreased.

Referring to FIGS. 9 and 10, there is shown another embodiment modified from the electrode construction shown in FIGS. 7 and 8. This electrode construction has an electrode 7 of a generally semicylindrical shape in place of the two electrodes 5 and 6 in FIGS. 7 and 8. This electrode 7 is such that the contacting area between the electrode 7 and the skin is at least twice that between the electrode 4 and the skin. In this case, it has been also found that the pain felt by a human being is decreased. Therefore, if the electrode construction is adapted such that the total contacting area between the skin and the electrode through which the negative voltage is applied is larger than that between the skin and the other electrode, the pain felt by a human being is decreased.

Each of the electrodes 3, 4 and 5 shown in FIGS. 7 to 8 comprises a hollow hemispherical member 10 of a conductive material such as iron or copper, as shown in FIGS. 11 and 12. The hollow hemispherical conductive member 10 has a plurality of perforations 11 provided therethrough as shown in FIG. 12 and a water-impregnating cover 12 made from a water-impregnating material such as sponge and cloth and applied to cover the outer surface of the conductive member. A mounting metal base 13 is water tightly fitted into the hollow conductive member 10 to form a hollow chamber 18, and a mounting sheath 14 is fitted onto a rod portion 15 of the metal base 13 to secure the water-impregnating cover 12 between a shoulder portion 16 of the metal base 13 and the mounting sheath so that the cover 12 is fitted over the hollow member 10. The metal base 13 has a female-threaded portion 17 provided at the lower end of the rod portion 15 and adapted to be screwed onto a male-thread (not shown) provided on the device housing so that the electrode is mounted on the device housing and connected to one of the output terminals of the blocking oscillator. The sizes of the hollow chamber 18 and the perforations 11 in the hollow hemispherical conductive member 10 are determined such that when the electrode is soaked in water sufficient water is stored in the hollow chamber 18 and when the device is in use the stored water exudes little by little through the perforations at a rate sufficient to keep the outer cover 12 in a ceaselessly wet condition, whereby good electric contact is at all times maintained between the electrode and the skin in contact therewith. Therefore, if the electrodes according to the present invention are used in a low frequency electronic therapy device, it is possible to give low frequency electric therapy to a human being without frequently soaking the electrodes in water.

What is claimed is:

1. A low frequency electronic therapy device adapted to apply a low frequency electric stimulus to a therapy point of a warm-blooded animal which device comprises a casing, a low frequency oscillator contained in said casing, said oscillator having output terminals, at least two electrodes electrically connected to the output terminals of the oscillator, said electrodes being adapted to be brought in contact with the skin at the therapy point, each of said electrodes including a hollow hemispherical conductive member having a mouth and a plurality of perforations therethrough and a mounting metal base water-tightly fitted into the mouth of said hollow member to form a hollow chamber in said hollow member for storing water therein, each of said mounting metal bases being mounted on the outside of said casing and electrically connected to a corresponding output terminal of said oscillator, a water-impregnating cover being applied to the outer surface of each of said conductive member covering said perforations, so that water stored in said hollow chamber exudes gradually through said perforations to impregnate said water impregnating cover, whereby said water impregnating cover is maintained impregnated with water to keep good electric contact between the electrode and the skin.

2. A low frequency electronic therapy device according to claim 1 characterized in that said water-impregnating cover is made from a material selected from the group consisting of sponge and cloth.

3. A low frequency electronic therapy device for applying a low frequency electric stimulus to a therapy point of a warm-blooded animal, which device comprises a casing; a low frequency oscillator located in said casing and having positive and negative output terminals; and a plurality of electrodes mounted on the outside of said casing adjacent to each other and adapted to be brought in contact with the skin of the animal about the therapy point, each of said electrodes being electrically connected to one of said output terminals of said oscillator, the electrodes connected to the negative output terminal through which a negative voltage is applied to the skin having a cumulative contacting area larger than that of all electrodes connected to the positive output terminal through which a positive voltage is applied to the skin.

4. A low frequency electronic therapy device according to claim 3 characterized in that one electrode connected to the negative output termnal through which a negative voltage is applied has a contacting area which is at least twice the contacting area of another electrode connected to the positive output terminal through which a positive voltage is applied to the skin.

5. A low frequency electronic therapy device according to claim 3 characterized in that there are at least two similar electrodes connected to the negative output terminal through which a negative voltage is applied to the skin, and one electrode similar to said two electrodes connected to the positive output terminal, through which a positive voltage is applied to the skin, so that the total contacting area between the skin and negative voltage applying electrodes is at least twice that between the skin and said positive voltage applying electrode.

6. A low frequency electronic therapy device according to claim 5 characterized in that each of said electrodes comprises a hollow hemispherical conductive member having a plurality of perforations therethrough and having a closed end and an opened end and a mounting metal base water-tightly fitted into said opened end of said hollow member to form a hollow chamber in said hollow member for storing water therein, each of said mounting metal basis being mounted on the outerside of said casing and electrically connected to a corresponding output terminal of said oscillator, a water-impregnating cover being applied to the outer surface of each said conductive member covering said perforations so that water stored in said hollow chamber exudes gradually through said perforations to impregnate said water impregnating cover, whereby said water impregnating cover is maintained impregnated with water to keep good electric contact between the electrode and the skin.

* * * * *